United States Patent [19]

Bayless

[11] Patent Number: 4,863,434
[45] Date of Patent: Sep. 5, 1989

[54] AUTOMATIC NEEDLE SHEATH FOR DISPOSABLE SYRINGE

[76] Inventor: William B. Bayless, 10131 Beverly Dr., Huntington Beach, Calif. 92646

[21] Appl. No.: 204,560

[22] Filed: Jun. 9, 1988

Related U.S. Application Data

[63] Continuation-in-part of Ser. No. 149,419, Jan. 29, 1988.

[51] Int. Cl.$^4$ ............................................. A61M 5/32
[52] U.S. Cl. ..................................... 604/198; 604/263
[58] Field of Search ............... 604/198, 192, 187, 263, 604/136

[56] References Cited

U.S. PATENT DOCUMENTS

| | | |
|---|---|---|
| 2,876,770 | 3/1959 | White . |
| 3,073,306 | 1/1963 | Linder . |
| 3,354,881 | 11/1967 | Bloch . |
| 4,139,009 | 2/1979 | Alvarez . |
| 4,573,976 | 3/1986 | Sampson et al. ..................... 604/198 |
| 4,581,025 | 4/1986 | Timmermans ....................... 604/264 |
| 4,610,667 | 9/1986 | Pedicano et al. ................... 604/192 |
| 4,631,057 | 12/1986 | Mitchell .............................. 604/198 |
| 4,654,034 | 3/1987 | Master et al. ....................... 604/192 |
| 4,659,330 | 4/1987 | Nelson et al. ....................... 604/192 |
| 4,664,654 | 5/1987 | Strauss ............................... 604/198 |
| 4,702,738 | 10/1987 | Spencer .............................. 604/198 |
| 4,702,739 | 10/1987 | Milorad .............................. 604/198 |

FOREIGN PATENT DOCUMENTS 1054316 2/1954 France ................................ 604/192

*Primary Examiner*—John D. Yasko
*Attorney, Agent, or Firm*—George J. Netter

[57] ABSTRACT

A hypodermic syringe and needle combination with a releasable, automatic needle enclosing sheath. A syringe barrel having an open and a closed end includes first and second longitudinally extending guide channels for guiding push rods secured to the thumb platform of a plunger rod. Ball-end engaging sockets are located at the ends of the guide channels for capturing ball-ends secured to the needle sheath which is slidably supported and displaceable between (1) a first position where the needle sheath is locked by engagement of the ball-ends in the sockets and which exposes the needle, and (2) a second position where the needle sheath encases the needle. The needle sheath is spring biased so that it travels from the first position to the second position when the ball-ends are released from the sockets by pressure applied on the thumb platform which causes the pushrods to push the ball-ends out of the sockets.

12 Claims, 2 Drawing Sheets

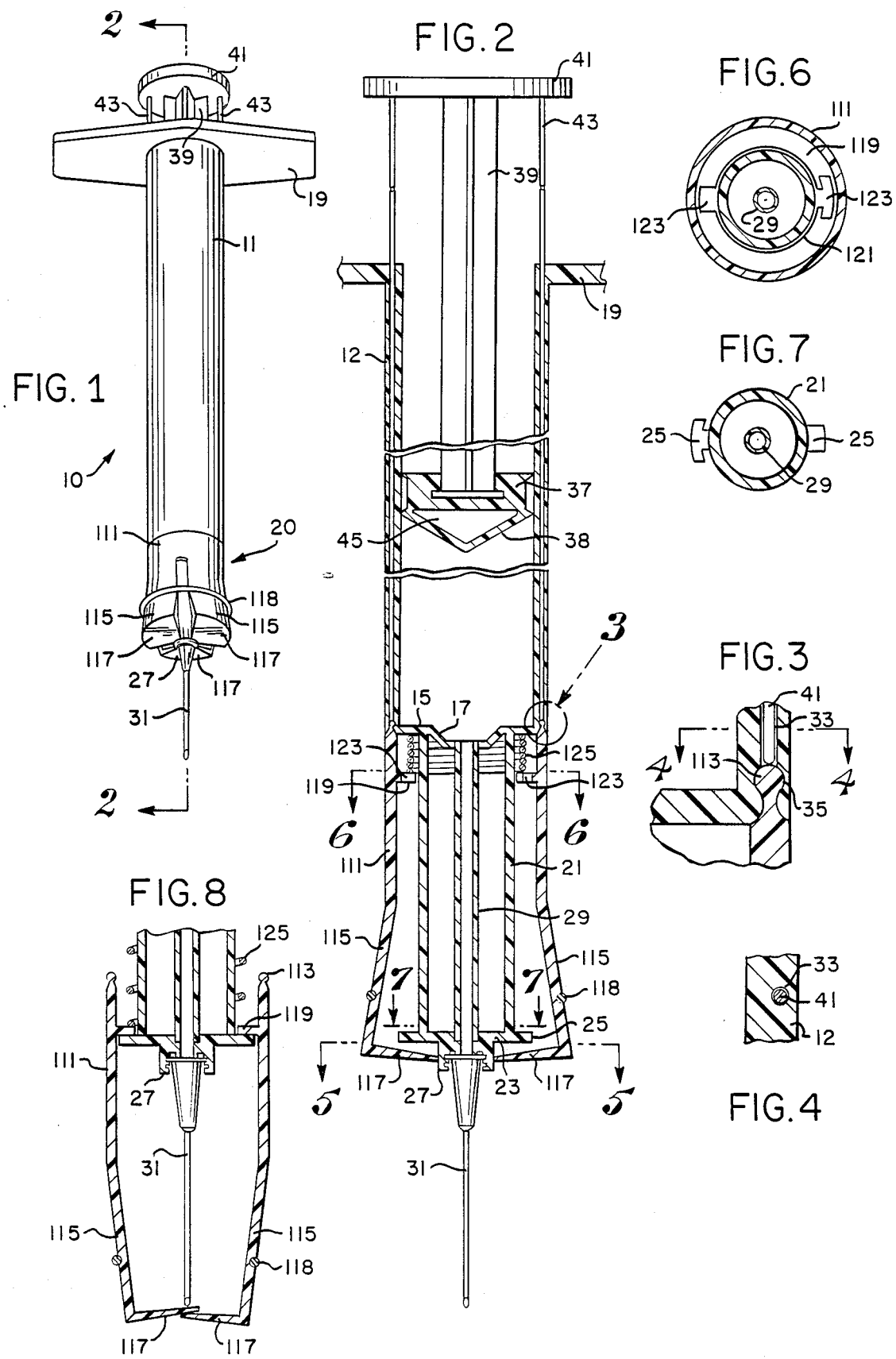

AUTOMATIC NEEDLE SHEATH FOR DISPOSABLE SYRINGE

This application is a continuation-in-part of application Ser. No. 149,419, filed Jan. 29, 1988.

BACKGROUND OF THE INVENTION

The disclosed invention generally relates to hypodermic syringes and needles, and is more particularly directed to a hypodermic syringe and needle combination having a needle sheath for enclosing the needle quickly and promptly after use.

Hypodermic syringes and needles have been used in the medical field for a long time. By design, hypodermic needles readily puncture skin, and medical personnel have been inadvertently pricked or wounded by the needles for many years. Unfortunately, inadvertent needle pricks and wounds can result in the transmission of infectious diseases, and the safe use and disposal of used syringes and needles is of great concern in the medical profession, particularly in light of the tragic consequences of acquired immunodeficiency syndrome (AIDS).

Known procedures for reducing the exposure to contaminated needles include the disposal of used syringes and needles into puncture resistant plastic containers, which are eventually sealed and disposed of. However, such procedure does not address the potential for accidents prior to disposal of the syringe and needle into the container. Moreover, such procedure cannot always be promptly followed, for example in emergency situations outside a medical facility as well as in a medical facility.

The apparatus of U.S. Pat. No. 4,702,738, issued to Spencer on Oct. 27, 1987, addresses the contaminated needle concern by providing a retractable sheath which can be locked in a needle covering position after use. However, positioning the sheath in the locked position requires the use of both hands, which in itself poses a risk of accidental wounding.

SUMMARY OF THE INVENTION

It would therefore be an advantage to provide a hypodermic syringe and needle which includes a needle sheath that is readily deployed with one hand to quickly enclose the needle after use.

The foregoing and other advantages and features are provided in a hypodermic syringe and needle combination which includes a syringe barrel having an open end and a closed end. A support barrel is attached to the closed end of the syringe barrel for supporting a needle sheath and for providing fluidic communication with the closed end of the syringe barrel; and a needle is coupled to the support barrel. A needle sheath is slidably supported on the support barrel and is displaceable between (1) a first position wherein the needle is exposed, and (2) a second position wherein the sheath encloses the needle. A locking structure locks the needle sheath in the first position, and a biasing spring biases the needle sheath toward the second position. Releasing apparatus for releasing the locking structure is secured to the finger actuated end of a fluid displacing plunger which is engaged in the syringe barrel. The locking structure is released pursuant to finger actuated release pressure on the plunger actuation end after administration of drug containing fluid, to allow the needle sheath to be displaced by the biasing spring to the second position to enclose the needle.

BRIEF DESCRIPTION OF THE DRAWING

The advantages and features of the disclosed invention will readily be appreciated by persons skilled in the art from the following detailed description when read in conjunction with the drawing wherein:

FIG. 1 is a perspective view of a hypodermic syringe and needle combination having a needle sheath in the open, needle-exposing position.

FIG. 2 is a sectional view taken along the section line 2 in FIG. 1.

FIG. 3 is a detail view showing the pushrod-released ball and socket arrangement for securing the needle sheath in the open position.

FIG. 4 is a partial sectional view taken along the section line 4 in FIG. 3.

FIG. 6 is a sectional view taken along the section line 6 if FIG. 2.

FIG. 7 is a sectional view taken along the section line 7 in FIG. 2.

FIG. 8 is a partial sectional view illustrating the needle sheath in a closed, needle-enclosing position.

DETAILED DESCRIPTION

Figure 5:
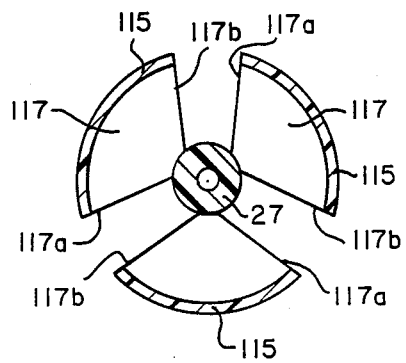
FIG. 5 is a sectional view taken along the section line 5 in FIG. 2.

In the following detailed description and in the several figures of the drawing, like elements are identified with like reference numerals.

Referring now to FIG. 1, illustrated therein is a hypodermic syringe and needle combination 10 which includes a primary syringe barrel 11 having a side wall 12 that forms a cylindrical bore 13. The cylindrical bore 13 extends from the open end of the syringe barrel 11 to the closed end of the primary syringe barrel 11 which includes an end wall 15. A centrally located recess 17 generally shaped like a truncated cone is formed in the end wall 15. Laterally extending finger flanges 19 are secured to the open end of the syringe barrel 11.

A secondary syringe barrel 21 of smaller diameter than the primary syringe barrel 11 has one end secured to the recessed end wall 15. The other end of the secondary syringe barrel 21 includes an end wall 23 and laterally extending locking keys 25. As discussed more fully herein, the locking keys 25 function to locate a needle sheath 20 and to prevent the needle sheath 20 from being removed after it has been deployed to encase the needle 31 of the hypodermic syringe and needle combination 10.

A standard needle support 27, for example one with internal threads, is secured to the end wall 23 of the secondary syringe barrel 21. A fluid channelling duct 29 extends from a centrally located opening in the recess 17 of the end wall 15 to an opening in the end wall 23, such opening extending through the needle support 27. The mounting end of a standard hypodermic needle 31 is coupled to the needle support 27, the needle 31 thus being in fluidic communication with the inside of the primary syringe barrel 11.

Diametrically opposite guide channels 33 are formed in the side wall 12 of the primary syringe barrel 11, parallel to the longitudinal axis of the cylindrical bore 13 and separated therefrom. The guide channels 33 extend from the open end of the syringe barrel 11 to locations near the end wall 15 at the closed end of the primary syringe barrel 11.

As shown in detail in FIG. 3, the ends of the guide channels 33 near the closed end of the primary syringe barrel 11 include ball capturing sockets 35 which are adapted to capture ball ends 113 secured to the needle sheath 20.

A sealing piston 37 having a generally conically shaped fluid engaging face 38 is secured to one end of a plunger rod 39, and is slidably engaged in the cylindrical bore 13 through the open end of the syringe barrel 11. A thumb platform 41 is secured to the other end of the plunger rod 39.

Diametrically opposite pushrods 43 are secured to the thumb platform 41 parallel to the plunger rod 39, and are configured to slide in the guide channels 33. The length of the pushrods 33 is chosen so that the unattached ends thereof are very close to the ball ends 113 captured in the sockets 35 when the sealing piston 37 has been completely slidably displaced against the recessed end wall 15 of the primary syringe barrel 11. This permits for conventional operation of the hypodermic syringe 10 in the administration of drug containing fluid without disengaging the captured ball ends 113 from the sockets 35.

The sealing piston 37 comprises a resilient material, for example rubber, and includes a generally conically shaped sealed chamber 45. When the sealing piston 37 is pressed against the recessed end wall 15 pursuant to actuation of the thumb platform 41 in the course of administration of drug containing fluid, the sealing piston 37 provides sufficient resistance to prevent deformation thereof, and the unattached ends of the pushrods 43 do not press against the ball ends 113 captured in the sockets 35.

Additional, greater pressure on the thumb platform 41 that overcomes the resistance of the resilient piston 37 will cause the pushrods 43 to engage and push the ball ends 113 of the needle sheath 20 out of the capturing sockets 35. Such release allows the biased needle sheath 20 to automatically fully encase the needle 31, as shown in FIG. 6.

The needle sheath 20 includes a generally cylindrical body 111 which is adapted to encompass the secondary syringe barrel 21. The end of the cylindrical body 111 closest to the primary syringe barrel 11 includes diametrically opposed ball ends 113 secured thereto, which are configured to engage the capturing sockets 35. Preferably, the ball ends 113 include, for example, parallel planar sides so that they can elastically deform upon insertion into the capturing sockets 35 without permanently deforming or breaking the sockets 35. When the ball ends 113 are engaged in the sockets 35, the needle 31 is exposed for use.

The needle sheath 20 further includes a closure assembly 30 secured to the end of the cylindrical body 111 furthest away from the primary syringe barrel 11, and can be formed integrally therewith. The closure assembly 30 includes three separated, resilient curved panels 115 symmetrically secured to the cylindrical body 111 and slightly separated from each other. The individual panels 115 are configured to slant inwardly toward the central axis of the cylindrical body 111 when no deforming forces are applied thereto. Inwardly projecting pie-section shaped leaves 117 are respectively secured to each of the panels 115. The leaves 117 are formed to slightly overlap laterally with at least one adjacent leaf when no deforming forces are applied to the leaves 117 and the panels 115. By way of specific example, as viewed in FIG. 5, the right linear edge 117a of each leaf 117 would slide over the the left linear edge 117b of the adjacent leaf 117. Each right linear edge 117 could be beveled to facilitate the overlapping action. The inner ends of the leaves 117 are recessed to facilitate being positioned over the outside of the needle support 27 as shown in FIGS. 2 and 5, and as discussed further herein. Such inner ends are further configured to overlap when no deformational forces are applied to the leaves 117 and the panels 115.

The panels 115 include respective circularly aligned recesses on their outside surfaces to accommodate a resilient O-ring 118, which insures that the leaves 117 overlap each other when no deforming forces are applied to the panels 115 and the leaves 117. The separation between the panels 115 should be small, large enough to ensure complete closure of the flaps 117.

The sheath 20 further includes a recessed internal flange 119 which includes a circular opening 121 and radially extending keyed openings 123. A coil spring 125 encircling the secondary syringe barrel 21 is compressed between the flange 115 and the recessed end wall 15 of the syringe barrel 11, and functions to bias the needle sheath 20 away from the closed end of the primary syringe barrel 11.

The circular opening 121 in the internal flange 119 is dimensioned to slidably encompass the secondary syringe barrel 21, and the keyed openings 123 are adapted to allow through passage of the locking keys 25 at the end of the secondary syringe barrel 21.

Preferably prior to coupling the needle 31 to the needle support 27, the needle sheath 20 is coupled to the primary syringe barrel 11 as follows. The coil spring 125 is placed around the secondary syringe barrel 21, and with the keyed openings 123 aligned with the locking keys 25, the locking keys 25 are passed through the keyed openings 123. After the internal flange 117 is clear of the locking keys 25, the needle sheath 20 is rotated, for example by 180 degrees, and then further displaced toward the primary syringe barrel 11 to engage the ball ends 113 in the capturing sockets 35 at the ends of the guide channels 33. The displacement of the needle sheath 20 toward the closed end of the primary syringe barrel 11 also compresses the coil spring 125. When the ball ends 30 are captured in the sockets 35, the leaves 117 are constrained in an open locked position by the needle support 27 as shown in FIG. 2.

After the needle sheath 20 is secured in the open locked position, the keyed openings 123 are no longer aligned with the locking keys 25, which function as a stop against the internal flange 117 when the needle sheath 20 is released, and further prevent the removal of the sheath 20 after it has been released.

The needle sheath 20 is of sufficient length to fully encase the longest needle to be utilized with a particular syringe, which in turn dictates the length of the secondary syringe barrel 21.

The sidewall 12 of the primary syringe barrel 11 and the elements secured thereto, including the recessed end wall 15, the finger flanges 19, the secondary syringe barrel 21, the end wall 23, the locking keys 25, and the needle support 27 can an integral unitary structure made, for example, of molded medical grade plastic.

Figure 9:
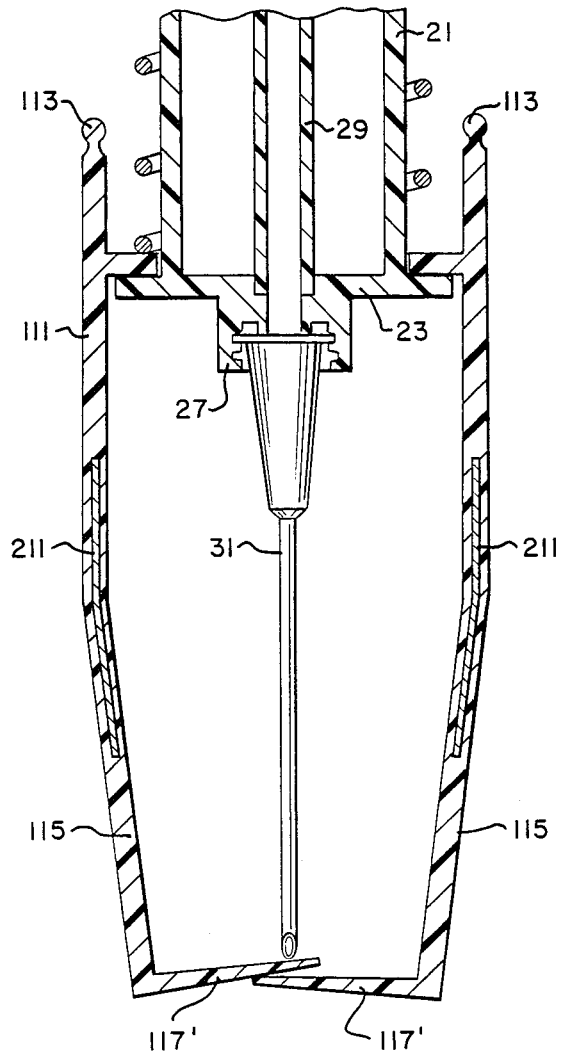
FIG. 9 is a partial sectional view illustrating a further embodiment of the needle sheath.

The elements of the needle sheath 20, except for the O-ring 118, can be an integral unitary structure made, for example, of molded plastic. With reference to FIG. 9, the needle sheath 20 can alternatively be molded plastic with imbedded resilient metal strips 211, comprising spring steel for example, which extend from the panels 115 into the cylindrical body 111. With such metal strips, the O-ring 118 would not be required to ensure the complete closure of the leaves 117.

The foregoing described hypodermic syringe and needle combination with needle sheath accepts a standard needle cover (not shown) when the needle sheath is in the open locked position, and can be distributed and stored in such configuration. For use, the needle cover is removed, and drug containing fluid is suctioned into the primary syringe barrel 11 in the conventional manner. The needle is inserted in the patient and the drug containing fluid is administered in a conventional manner, for example, by the application of thumb pressure on the thumb platform 41 while supporting the finger flanges 19 with two fingers. After the drug containing fluid is administered, the thumb and finger positions on the thumb platform 41 and the finger flanges 19 are maintained while the needle is removed from the patient. After the needle has been removed from the patient, application of thumb pressure on the thumb platform 41 greater than the pressure used for drug administration causes the ball ends 113 to be released from the sockets 35, allowing the biased needle sheath 20 to slide over the needle 31 and encase it.

The foregoing hypodermic syringe and needle combination with needle sheath advantageously allows for one-hand deployment of the needle sheath, which can be achieved with the same thumb and finger positioning as that used for administering the drug containing fluid. Such deployment of the needle sheath can be controlled to occur promptly after use of the hypodermic syringe and needle combination. As a result, risk of accidental wounding with used contaminated needles is significantly reduced.

Although the foregoing has been a description and illustration of specific embodiments of the invention, various modifications and changes thereto can be made by persons skilled in the art without departing from the scope and spirit of the invention as defined by the following claims.

What is claimed is:

1. A hypodermic syringe and needle comprising:
   a syringe barrel having an open end and a closed end;
   support means attached to the closed end of said syringe barrel for supporting a needle sheath and for providing fluidic communication with the closed end of said syringe barrel;
   a hypodermic needle coupled to said support means;
   a needle sheath slidably supported by said support means including at one end a closure for enclosing said needle when not constrained in an open position, said needle sheath being displaceable between (1) a first position wherein said closure is constrained in an open position with said needle exposed, and (2) a second position wherein said closure is closed and encases said needle;
   locking means for locking said needle sheath in said first position;
   biasing means for biasing said needle sheath away from the closed end of said syringe barrel;
   a fluid displacing plunger having at one end a sealing position slidably engaged in said syringe barrel and further having a finger actuation end, whereby drug containing fluid is administered pursuant to finger actuated displacement of said plunger to the closed end of said syringe barrel; and
   release means coupled to said actuation end of said plunger for controllably releasing said locking means pursuant to finger actuated release pressure on said actuation end after administration of drug containing fluid, to allow said needle sheath to be displaced by said biasing means along said support means and along said needle to said second position to fully enclose said needle.

2. The hypodermic syringe and needle combination of claim 1 wherein said locking means includes selectively engageable mating components attached to said syringe barrel and said needle sheath.

3. The hypodermic syringe and needle combination of claim 2 wherein said selectively engageable mating components comprise a socket and a ball-end engageable in said socket.

4. The hypodermic syringe and needle combination of claim 3 wherein said release means comprises means for disengaging said ball-end from said socket.

5. The hypodermic syringe and needle combination of claim 4 wherein said means for disengaging comprises a pushrod connected to the finger actuation end of said fluid displacing plunger.

6. The hypodermic syringe and needle combination of claim 5 wherein said syringe barrel includes a guide channel extending from a location adjacent its open end to a location adjacent its closed end for guiding said pushrod.

7. The hypodermic syringe and needle combination of claim 6 wherein said socket is at the end of said guide channel adjacent the closed end of said syringe barrel, and wherein said ball-end is secured to said needle sheath.

8. The hypodermic syringe and needle combination of claim 1 wherein said closure includes a plurality of leaves which overlap one another when not constrained in an open position.

9. The hypodermic syringe and needle combination of claim 8 wherein said leaves are constrained in an open position by said support means when said needle sheath is in said first position.

10. A hypodermic syringe and needle comprising:
    a syringe barrel having an open end and a closed end;
    support means attached to the closed end of said syringe barrel for supporting a needle sheath and for providing fluidic communication with the closed end of said syringe barrel;
    a hypodermic needle coupled to said support means;
    a needle sheath slidably supported by said support means including at one end a closure for enclosing said needle when not constrained in an open position, said needle sheath being displaceable between (1) a first position wherein said closure is constrained in an open position with said needle exposed, and (2) a second position wherein said closure is closed and encases said needle;
    first and second ball-end and socket connectors secured to the closed end of said syringe barrel and to said needle sheath for locking said needle sheath in said first position;
    biasing means for biasing said needle sheath away from the closed end of said syringe barrel;
    a fluid displacing plunger having at one end a sealing position slidably engaged in said syringe barrel and further having a finger actuation end, whereby drug containing fluid is administered pursuant to finger actuated displacement of said plunger to the closed end of said syringe barrel;
    first and second pushrods coupled to said actuation end of said plunger for controllably releasing said first and second mating ball-end and socket connectors pursuant to finger actuated release pressure on said actuation end after administration of drug containing fluid, to allow said needle sheath to be displaced by said biasing means along said support means and along said needle to said second position to fully enclose said needle.

11. The hypodermic syringe and needle combination of claim 10 wherein said syringe barrel includes first and second guide channels extending from a location adjacent its open end to a location adjacent its closed end for guiding said first and second pushrods.

12. The hypodermic syringe and needle combination of claim 11 wherein said first and second ball-end and socket connectors comprise:
  first and second sockets at the ends of said first and second guide channels adjacent the closed end of said syringe barrel; and
  first and second ball-ends secured to said needle sheath and adapted to be engageable in said first and second sockets.

* * * * *